United States Patent [19]

Meilland

[11] Patent Number: Plant 5,694

[45] Date of Patent: Mar. 18, 1986

[54] ROSE PLANT—MEIROPE VARIETY

[75] Inventor: Marie L. Meilland, Antibes, France

[73] Assignee: The Conard-Pyle Company, West Grove, Pa.

[21] Appl. No.: 622,122

[22] Filed: Jun. 19, 1984

[51] Int. Cl.[4] ..... A01H 5/00

[52] U.S. Cl. ..... Plt./16

[58] Field of Search ..... Plt./16

*Primary Examiner*—Robert E. Bagwill

*Attorney, Agent, or Firm*—Burns, Doane, Swecker & Mathis

[57] ABSTRACT

A new and distinct variety of Hybrid Tea rose plant is provided having fully double blossoms which are of an attractive intense orange coloration on the upper surfaces of the petals. The new variety is well adapted for the production of cut flowers on an abundant basis while being grown under greenhouse conditions. Once cut the blossoms ship well and exhibit good vase life.

17 Drawing Figures

SUMMARY OF THE INVENTION

The new and distinct variety of Hybrid Tea rose plant of the invention was created by artificial pollination wherein two parents were crossed which previously had been studied for the characteristics sought. The seed parent resulted from the artificial pollination of the Meidanu variety (non-patented) by the product of the artificial pollination of the Meihand and Meialfi varieties (each non-patented). The pollen parent of the new variety was an unnamed seedling. The parentage of the new variety can be summarized as follows:

[Meidanu × (Meihand × Meialfi)] × unnamed seedling.

The seeds resulting from the above pollination were sown and plantlets were obtained which were physically and biologically different from each other. Selective study resulted in the identification of a single plant of the new variety. The desirable qualities of the new variety have been confirmed through extensive testing, and the importance of the new variety has been firmly established.

It was found that the new variety of Hybrid Tea rose plant of the present invention possesses the following combination of characteristics:

(a) from the physical point of view, the plant has bronze green adult wood, an upright growth habit, and forms attractive double blossoms which are intense orange on the inner surfaces with the outer surfaces of the petals being orange fading to orange blended with pink, and (b) from a biological point of view the plant has vigorous vegetation, flowers abundantly and continuously when grown under greenhouse conditions, and exhibits good resistance to diseases.

The new variety is well adapted to grow under greenhouse conditions where it can be relied upon to force well and to abundantly yield attractive orange blossoms.

The blossoms of the new variety have been found to exhibit good shipping qualities, and to exhibit a good vase life.

The new variety has been found to undergo asexual propagation by a number of means and may be grown on any one of a number of rootstocks. The characteristics of the new variety have been found to be strictly transmissible by such asexual propagation from one generation to another.

The rose plant of the new variety has been named the Meirope variety.

BRIEF DESCRIPTION OF THE PHOTOGRAPH

The accompanying photograph shows as nearly true as it is reasonably possible to make the same in a color illustration of this character, typical specimens of plant parts of the new variety when observed during September. The rose plants of the new variety described herein were grown at Cap d'Antibes, France, in a greenhouse and were grafted on *Rosa indica* rootstock.

DETAILED DESCRIPTION

Figures 1, 2, 3, 4, 5, 6, 7, 8, 9, 10, 11, 12, 13, 14, 15, 16, 17:
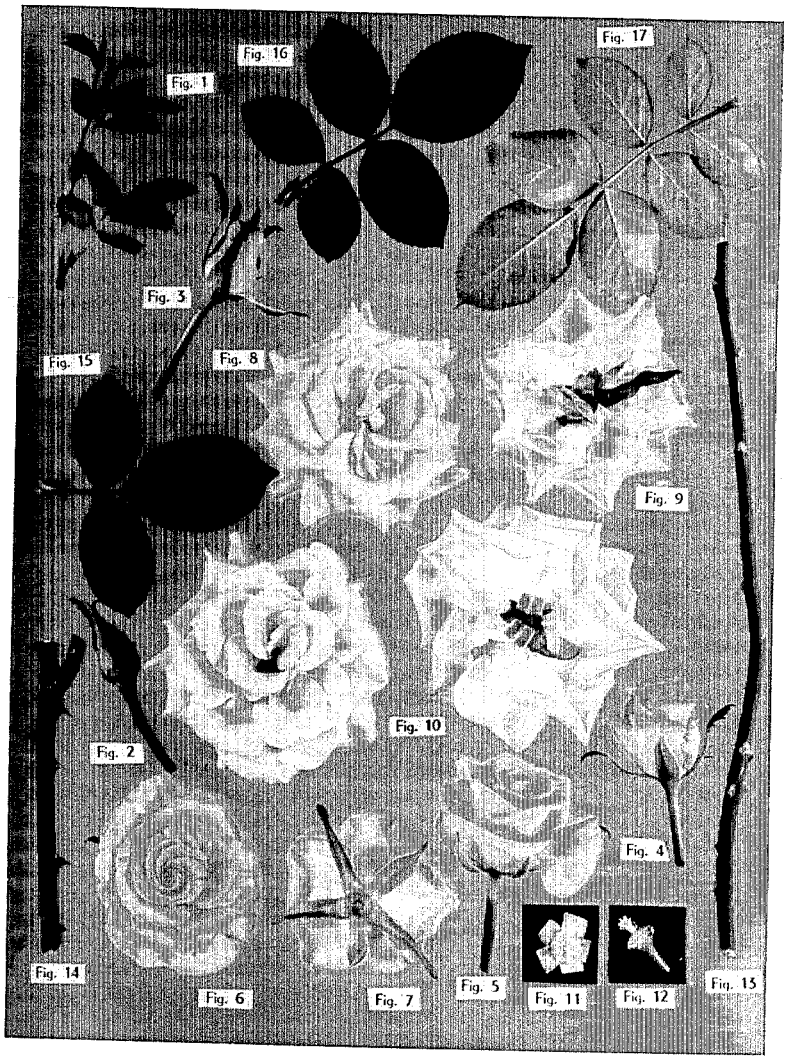
FIG. 1 illustrates a specimen of a young shoot.
FIG. 2 illustrates a specimen of a flowering bud before the opening of the sepals.
FIG. 3 illustrates a specimen of a flowering bud at the opening of the sepals.
FIG. 4 illustrates a specimen of a flowering bud at the opening of the petals.
FIG. 5 illustrates a specimen of a flower at the beginning of opening.
FIG. 6 illustrates a specimen of a flower in the course of opening—plan view—obverse.
FIG. 7 illustrates a specimen of a flower in the course of opening—plan view—reverse.
FIG. 8 illustrates a specimen of a fully open flower—plan view—obverse.
FIG. 9 illustrates a specimen of a fully open flower—plan view—reverse.
FIG. 10 illustrates on the left a specimen fully open flower prior to petal drop—plan view—obverse wherein the final coloration is shown, and illustrates on the right a specimen of a fully open flower prior to petal drop—plan view—reverse wherein the final coloration is shown.
FIG. 11 illustrates a specimen of a floral receptacle showing the arrangement of the stamens and pistils.
FIG. 12 illustrates a specimen of a floral receptacle showing the arrangement of the pistils (sepals and stamens removed)
FIG. 13 illustrates a specimen of a young flowering stem.
FIG. 14 illustrates a specimen of a main branch.
FIG. 15 illustrates a specimen of a leaf with three leaflets—upper surface.
FIG. 16 illustrates a specimen of a leaf with five leaflets—upper surface.
FIG. 17 illustrates a specimen of a leaf with seven leaflets—under surface.

The chart used in the identification of colors is that of The Royal Horticultural Society (R.H.S. Colour Chart). The terminology preceding the numbered references has been added to designate in common terms the corresponding colors. The rose plants of the new variety described herein were grown at Cap d'Antibes, France, in a greenhouse while grafted on *Rosa indicia* rootstock and were observed during September.

Class: Hybrid tea.

Plant:

*Height.*—When plants are pruned to 85 cm., flower-bearing stems of approximately 35 to 65 cm. in length are produced.

*Habit.*—Upright. Branches:

Color.—Young stems: Light green, Yellow-Green Group 146C, somewhat shaded with brownish red. Mature wood: Bronze green, Yellow-Green Group 146A.

*Thorns.*—Shape: Upper edge: Straight with a slight curve which is inflected toward the base. Lower edge: Concave. Size: Medium on the flower bearing stems and large on the adult wood. Quantity: Not very numerous and sometimes even non-existent on the flower bearing stems, but numerous on the mature wood. Color: On young stems: Reddish. On mature wood: Green blended with pink and havana brown.

Leaves:

*Stipules.*—Large and linear.

*Petioles.*—Inner surface: Reddish brown on young foliage and medium green on adult foliage. Outer surface: Light green with several small thorns.

*Leaflets.*—Number: 3 and 5 (most often) and sometimes 7. Shape: Generally oval, but from time to time they are elliptic. Serration: Simple and regular. Texture: Rough. General effect: Foliage is ample and dense, and has a somewhat dull cast. Color: Young foliage: Upper surface: Reddish brown. Under surface: Reddish. Color: Adult foliage: Upper surface; Dark green, Yellow-Green Group 147A. Under surface: Medium green, Yellow-Green Group 147B.

Inflorescence:

*Number of flowers.*—Generally one per stem when grown under greenhouse forcing conditions.

*Penduncle.*—Straight, rigid, and has glandular thorns, its length is approximately 7 cm. on average.

*Sepals.*—Upper surface: Tomentose, greenish in coloration. Under surface: Medium green with shades of red, often bearing small thorn-like growths.

*Bud.*—Shape: Conical. Length: Approximately 2.5 cm. on average. Size: Medium. Color: When opening: Upper surface: Orange, Orange-Red Group 32A. Under surface: Mandarin orange, Red Group 40B, fading to Mandarin orange, Red Group 40C, toward the base.

*Flower.*—Form: Fully double, initially the sides are substantially parallel and subsequently a fully open flat configuration is assumed. Diameter: Approximately 8 cm. on average. Color when opening begins: Upper surface: Intense orange, Orange-Red Group 32B. Under surface: Orange, Orange-Red Group 33C. Color: When partially open: Upper surface: Intense orange, Orange-Red Group 32B. Under surface: Orange, Orange-Red Group 33C. Color: At end of opening: Upper surface: Light orange. Under surface: Orange, Orange-Red Group 33C, somewhat suffused on the petal margin with pink, Red Group 52C, and fading at the end of the cycle. Fragrance: None. Lasting quality: Long. Stamens: Number: Approximately 72 on average. Anthers: Normal and yellowish in coloration. Pistils: Number: Approximately 35 on average. Stigmas: Yellowish in coloration. Styles: Straw colored. Recepacle: Light green in coloration.

Development:

*Vegetation.*—Vigorous.

*Blossoming.*—Abundant and continuous under greenhouse conditions.

*Aptitude to greenhouse forcing.*—Good.

*Disease resistance.*—Good.

I claim:

1. A new and distinct variety of Hybrid Tea rose plant characterized by the fact that:

(a) from the physical point of view, the plant has bronze green adult wood, an upright growth habit, and forms attractive double blossoms which are intense orange on the inner surfaces with the outer surfaces of the petals being orange fading to orange blended with pink, and (b) from a biological point of view the plant has vigorous vegetation, flowers abundantly and continuously when grown under greenhouse conditions, and exhibits good resistance to diseases, substantially as herein shown and described.

* * * * *